US010585146B2

(12) United States Patent
Christensen et al.

(10) Patent No.: US 10,585,146 B2
(45) Date of Patent: Mar. 10, 2020

(54) SYSTEM FOR PROVIDING AN EXCITATION SIGNAL TO AN ELECTROCHEMICAL SYSTEM AND METHOD THEREFOR

(71) Applicant: Lithium Balance A/S, Ishøj (DK)

(72) Inventors: Andreas Elkjær Christensen, Ishøj (DK); Rasmus Mosbæk, Ishøj (DK)

(73) Assignee: Lithium Balance A/S, Ishøj (DK)

( * ) Notice: Subject to any disclaimer, the term of this patent is extended or adjusted under 35 U.S.C. 154(b) by 0 days.

(21) Appl. No.: 15/742,757

(22) PCT Filed: Jul. 8, 2016

(86) PCT No.: PCT/EP2016/066287
§ 371 (c)(1),
(2) Date: Jan. 8, 2018

(87) PCT Pub. No.: WO2017/005904
PCT Pub. Date: Jan. 12, 2017

(65) Prior Publication Data
US 2018/0203073 A1 Jul. 19, 2018

(30) Foreign Application Priority Data
Jul. 9, 2015 (DK) ................................ 2015 00405

(51) Int. Cl.
G01R 31/389 (2019.01)
G01R 31/00 (2006.01)
G01N 27/26 (2006.01)

(52) U.S. Cl.
CPC ........... *G01R 31/389* (2019.01); *G01N 27/26* (2013.01); *G01R 31/007* (2013.01)

(58) Field of Classification Search
CPC ..... G01R 31/389; G01R 31/007; G01N 27/26
(Continued)

(56) References Cited

U.S. PATENT DOCUMENTS 6,037,777 A * 3/2000 Champlin ............ G01R 31/367
324/430
6,208,147 B1 * 3/2001 Yoon .................. G01R 31/3842
324/430

(Continued)

FOREIGN PATENT DOCUMENTS

FR 2923023 A1 5/2009
WO 2012025706 A1 3/2012
WO 2015014764 A2 2/2015

*Primary Examiner* — Christopher P McAndrew
(74) *Attorney, Agent, or Firm* — Dinsmore & Shohl LLP

(57) ABSTRACT

A vehicle system provides an excitation signal to an electrochemical system for use in Electrochemical Impedance Spectroscopy diagnostics. The electrochemical system is connectable to the vehicle system and the vehicle system includes a power stage, such as a charger, connectable to the electrochemical system for supplying electrical energy to the electrochemical system, and/or connectable to the electrochemical system for withdrawing electrical energy from the electrochemical system, and an Excitation Generation Unit comprised by the power stage or operatively connected to the power stage. The Excitation Generation Unit is adapted for instructing the power stage to generate an excitation signal for use in the Electrochemical Impedance Spectroscopy diagnostics, and the power stage is adapted for generating the excitation signal and supplying the excitation signal to the electrochemical system when so instructed by the Excitation Generation Unit. A method provides an excitation signal to an electrochemical system using the vehicle system.

9 Claims, 2 Drawing Sheets

Figure 1:
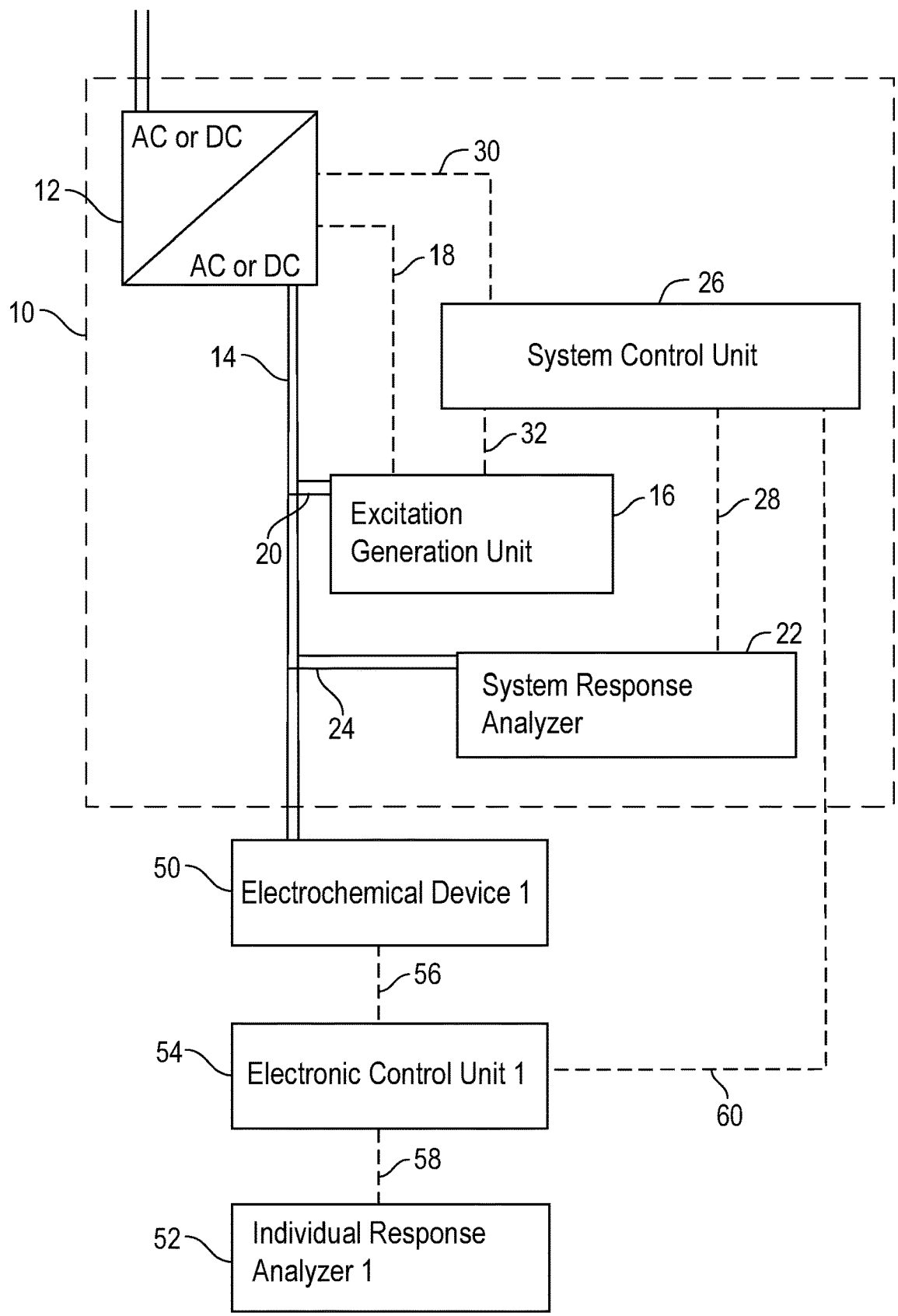

(58) Field of Classification Search
USPC .......................................................... 324/430
See application file for complete search history.

(56) References Cited

U.S. PATENT DOCUMENTS

| | | | | |
|---|---|---|---|---|
| 6,850,037 | B2* | 2/2005 | Bertness | G01R 31/36 |
| | | | | 320/132 |
| 7,688,074 | B2* | 3/2010 | Cox | B60W 20/12 |
| | | | | 324/426 |
| 7,705,602 | B2* | 4/2010 | Bertness | G01R 31/007 |
| | | | | 324/426 |
| 7,706,991 | B2* | 4/2010 | Bertness | G01R 31/343 |
| | | | | 320/104 |
| 7,723,993 | B2* | 5/2010 | Klang | G01R 31/387 |
| | | | | 324/431 |
| 8,513,949 | B2* | 8/2013 | Bertness | G01R 31/3648 |
| | | | | 324/426 |
| 9,317,055 | B2* | 4/2016 | Egami | G05F 1/66 |
| 2002/0196027 | A1 | 12/2002 | Tate et al. | |
| 2007/0069734 | A1* | 3/2007 | Bertness | G01R 31/007 |
| | | | | 324/411 |
| 2011/0089907 | A1 | 4/2011 | Bhardwaj et al. | |
| 2012/0019253 | A1* | 1/2012 | Ziegler | H01M 10/48 |
| | | | | 324/433 |
| 2012/0078552 | A1* | 3/2012 | Mingant | G01R 31/367 |
| | | | | 702/63 |
| 2012/0303208 | A1* | 11/2012 | Hariharan | H01M 10/48 |
| | | | | 701/32.9 |
| 2012/0306504 | A1* | 12/2012 | van Lammeren | G01R 31/396 |
| | | | | 324/430 |
| 2012/0316815 | A1* | 12/2012 | Morigaki | G01R 31/392 |
| | | | | 702/63 |
| 2013/0013236 | A1* | 1/2013 | Takahashi | G01R 31/367 |
| | | | | 702/63 |
| 2013/0063094 | A1* | 3/2013 | Gibbs | H01M 10/441 |
| | | | | 320/134 |
| 2013/0141109 | A1* | 6/2013 | Love | G01R 31/382 |
| | | | | 324/430 |
| 2013/0229156 | A1* | 9/2013 | Brandon | B60L 3/0046 |
| | | | | 320/136 |
| 2014/0117938 | A1 | 5/2014 | Ouzaarou et al. | |
| 2014/0300363 | A1* | 10/2014 | Thomas | G01R 31/382 |
| | | | | 324/426 |
| 2014/0358462 | A1* | 12/2014 | Christophersen | G01R 31/389 |
| | | | | 702/65 |
| 2015/0072198 | A1* | 3/2015 | Fink | H01M 10/48 |
| | | | | 429/90 |

* cited by examiner

SYSTEM FOR PROVIDING AN EXCITATION SIGNAL TO AN ELECTROCHEMICAL SYSTEM AND METHOD THEREFOR

CROSS-REFERENCE TO RELATED APPLICATIONS

This application is the U.S. national stage of PCT/EP2016/066287 filed Jul. 8, 2016, which claims priority of Denmark Patent Application PA 2015 00405 filed Jul. 9, 2015 of which is hereby incorporated by reference in its entirety.

The present invention pertains to the generation of excitation signals for use in diagnostics of electrochemical devices by means of Electrochemical Impedance Spectroscopy.

Electrochemical Impedance Spectroscopy is a technique in which an excitation signal is applied to an electrochemical system for eliciting a response signal from the electrochemical system. The response signal can then be measured to obtain information, such as diagnostic information, of the electrochemical system. Electrochemical Impedance Spectroscopy is inter alia described in Orazem, M. E. & Tribollet, B. *Electrochemical Impedance Spectroscopy*. (John Wiley & Sons, 2008). The excitation signal is normally a current signal or a voltage signal applied to the terminals of the measured system, and the waveform of the excitation signal can be sinusoidal with single or multiple frequencies, time-domain impulses or steps.

Electrochemical Impedance Spectroscopy can be used for diagnosis of electrochemical devices including, but not limited to, batteries, fuel cells, capacitors, photovoltaics, photoelectrochemical cells, electrolysis cells, see for example Birkl, C. R. & Howey, D. a. *Model identification and parameter estimation for LiFePO 4 batteries*. IET Hybrid Electr. Veh. Conf. 2013, HEVC 2013 1-6 (2013), Deng, Z. et al. *Electrochemical Impedance Spectroscopy Study of a Lithium/Sulfur Battery: Modeling and Analysis of Capacity Fading*. J. Electrochem. Soc. 160, 553-558 (2013), Jensen, S. H., Hauch, A., Knibbe, R., Jacobsen, T. & Mogensen, M. Modeling Degradation in SOEC Impedance Spectra. J. Electrochem. Soc. 160, F244-F250 (2013), Mosbaek, R. R., Hjelm, J., Barfod, R., Høgh, J., & Hendriksen, P. V. *Electrochemical Characterization and Degradation Analysis of Large SOFC Stacks by Impedance Spectroscopy*. Fuel Cells, 13(4), 605-611 (2013), Lopes, T., Andrade, L., Ribeiro, H. A. & Mendes, A. *Characterization of photoelectrochemical cells for water splitting by Electrochemical Impedance Spectroscopy*. Int. J. Hydrogen Energy 35, 11601-11608 (2010), Taberna, P. L., Simon, P. & Fauvarque, J. F. *Electrochemical Characteristics and Impedance Spectroscopy Studies of Carbon-Carbon Supercapacitors*. J. Electrochem. Soc. 150, A292 (2003), Leever, B. J., Bailey, C. a., Marks, T. J., Hersam, M. C. & Durstock, M. F. *In situ characterization of lifetime and morphology in operating bulk heterojunction organic photovoltaic devices by impedance spectroscopy*. Adv. Energy Mater. 2, 120-128 (2012), and Fabreqat-Santiaqo, F. et al. *Correlation between photovoltaic performance and impedance spectroscopy of dye-sensitized solar cells based on ionic liquids*. J. Phys. Chem. C 111, 6550-6560 (2007).

The diagnostics may comprise determining various parameters of the electrochemical system, for example as described in Buller, S., Thele, M., Karden, E. & De Doncker, R. W. *Impedance-based non-linear dynamic battery modeling for automotive applications*. J. Power Sources 113, 422-430 (2003), Ender, M., Weber, A. & Ivers-Tiffée, E. *Analysis of Three-Electrode Setups for AC-Impedance Measurements on Lithium-Ion Cells by FEM simulations*. J. Electrochem. Soc. 159, A128 (2012), J. Morrison, W. Morrison, and J. Christophersen, Method of detecting system function by measuring frequency response US Patent 20 100 274 510, (2010), Huet F. *A review of impedance measurements for determination of the state-of-charge or state-of-health of secondary batteries*. J. Power Sources 70, 59-69 (1998), Itagaki, M., Honda, K., Hoshi, Y. & Shitanda, I. *In-situ EIS to determine impedance spectra of lithium-ion rechargeable batteries during charge and discharge cycle*. J. Electroanal. Chem. 1-7 (2014), Jespersen, J. *Capacity measurements of Li-ion batteries using AC impedance spectroscopy*. World Electr. Veh. J. 3, (2009), Lvovich, V., Wu, J., Bennett, W., Demattia, B. & Miller, T. *Applications of AC Impedance Spectroscopy as Characterization and Diagnostic Tool in Li-Metal Battery Cells*. ECS Trans. 58, 1-14 (2014), and Mauracher, P. & Karden, E. *Dynamic modelling of lead/acid batteries using impedance spectroscopy for parameter identification*. J. Power Sources 67, 69-84 (1997).

The excitation signal used for Electrochemical Impedance Spectroscopy may be implemented by different means, see R. Robinson, *System noise as a signal source for impedance measurements on batteries connected to operating equipment*. Journal of Power Sources, vol. 42, no. 3, pp. 381-388, (1993), Howey, D. A., Mitcheson, P. D., Yufit, V., Offer, G. J. & Brandon, N. P. *Online measurement of battery impedance using motor controller excitation*. IEEE Trans. Veh. Technol. 63, 2557-2566 (2014), Troeltzsch, U. & Kanoun, O. C. 1-*Miniaturized Impedance Measurement System for Battery Diagnosis*. Proc. Sens. 2009, Vol. I 251-256 (2009), Beer, C. De, Barendse, P., Pillay, P., Pullecks, B. & Rengaswamy, R. *Online fault diagnostics and impedance signature mapping of High Temperature PEM fuel cells using rapid small signal injection*. Electrochim. Acta 35, 1798-1803 (1990), and Xie, C. J., Liu, J. B. & Zhao, H. B. *AC-DC Isolation of EIS Impedance Test System for Li-Ion Battery Packs*. Adv. Mater. Res. 823, 509-512 (2013).

One promising application of Electrochemical Impedance Spectroscopy is for obtaining parameters such as State-of-Charge (SoC) and State-of-Health (SoH) of batteries used in Electrical Vehicles. In applications like this it is paramount to be able of having an accurate measure of remaining charge in the batteries in order to make an accurate prediction of remaining range for the electrical vehicle.

The same considerations apply for nearly every conceivable system in which energy is stored in electrochemical systems, be it in the shape of smaller lithium-ion batteries in cell-phones or computers, or larger batteries used for grid storage.

One drawback of Electrochemical Impedance Spectroscopy is that the technique adds further cost and complexity to the already high cost of the electrochemical system itself including the therewith associated auxiliary equipment such as the Battery Management System and other control electronics.

Thus, one on one hand wider adoption of electrochemical systems as bearers of energy, in particular in electrical vehicles, may be hampered by the inaccuracy in determining the state of the electrochemical system, e.g. State-of-Charge and State-of-Health, using techniques other than Electrochemical Impedance Spectroscopy.

On the other hand the implementation of Electrochemical Impedance Spectroscopy could also hinder wider adoption of for example electric vehicles due to the increase in cost of the electrochemical system, i.e. the batteries needed to power the electric vehicle.

It is therefore an object of the present invention to provide a system and a method which lower the cost and/or complexity of diagnosis of electrochemical systems by Electrochemical Impedance Spectroscopy.

It is a further object of the present invention to provide a system and a method for providing excitation signals for use in Electrochemical Impedance Spectroscopy at in a simpler way and/or at a lower cost.

At least one of the above objects, or at least one of the further objects which will be evident from the below description of the present invention, is according to the first and second aspects of the present invention achieved by a system for providing an excitation signal to an electrochemical system as described herein and a method of providing an excitation signal to an electrochemical system as described herein.

By using the power stage to generate and supply the excitation signal, when instructed to do so by the Excitation Generation Unit, the already present power electronics comprised by the power stage can now be used also for the generation and supply of excitation signals, thus decreasing the cost and complexity of obtaining diagnosis of the electrochemical system by Electrochemical Impedance Spectroscopy. This is in contrast to using a prior art Excitation Generation Unit in which all components needed for generating the excitation signal are provided in the Excitation Generation Unit and which leads to an increased cost and complexity. In the system according to the first aspect of the present invention some of the already present power electronics in the power stage can now be used for the primary purpose, i.e. supplying electrical energy to the electrochemical system or withdrawing electrical energy therefrom, and, when needed, also for the secondary purpose of generating and supplying the excitation signal, thus reducing the number of components needed for the two purposes.

Further, as the power stage and the Excitation Generation Unit are part of the system, and not part of the electrochemical system, the cost of the electrochemical system is decreased as each electrochemical system can be excited for the purpose of Electrochemical Impedance Spectroscopy diagnostics when each electrochemical system is connected to the system.

This obviates the need of including an Excitation Generation Unit in each electrochemical system, thus further lowering costs.

In the case of the electrochemical system being a battery used in an electrical vehicle, and the system being comprised by a charging station for the electrical vehicle, the above may for example enable a lower cost implementation of service tools, i.e. servicing and diagnostics of the battery in the electrical vehicle, and fleet management, as more of the existing components are used. Further, in this case a single charging station may be used with a plurality of electrical vehicles for facilitating Electrochemical Impedance Spectroscopy diagnostics on a plurality of electrochemical systems in the plurality of electrical vehicles.

In the context of the present invention the term electrochemical system covers both a single electrochemical device, i.e. a single electrochemical cell or unit, and a collection of multiple electrochemical devices, e.g. cells, connected electrically in either series, parallel or a combination thereof.

Electrochemical Impedance Spectroscopy (EIS) is a technique for characterising electrochemical systems and for obtaining diagnostics on the systems. The technique uses the injection of an electrical signal, i.e. excitation signal, and an analysis of the resultant response signal. The injected signal, or excitation, can have many types of waveform, typically single- or multi-frequency sinusoidal signals or time-domain impulses or steps are used, see Barsoukov, E., Ryu, S. H. & Lee, H. *A novel impedance spectrometer based on carrier function Laplace-transform of the response to arbitrary excitation*. J. Electroanal. Chem. 536, 109-122 (2002). The excitation signal can either be a voltage or current signal.

If the excitation is sufficiently small the measured response can be used to calculate the impedance of the system. The small excitation is mainly necessary due to the linear approximation, but for certain electrochemical devices, the system may also change state if the excitation is not kept sufficiently small. Due to the time dependent nature of the excitation there might be a phase change in the measured system and the complex resistance, or impedance $Z(\omega)$, can be found from Ohms law when written using complex notation if the voltage and current is given by:

$$U(\omega)=U_0 \cdot e^{j\omega t} \text{ and } I(\omega)=I_0 \cdot e^{j(\omega t-\phi)}.$$

From which it follows that the impedance is:

$$Z(\omega) = \frac{U(\omega)}{I(\omega)} = \frac{U_0}{I_0} \cdot e^{j\phi}$$

$$Z(\omega) = |Z| \cdot e^{j\phi} = R_{real} + j \cdot R_{img}$$

Changing the excitation frequency of the sinusoidal input signal results in a changed angular frequency, $\omega$ as $\omega=2\pi f$. The resulting impedance spectrum, for $Z(\omega)$ over the tested frequency range, can provide information on the condition of the electrodes and be used to quantify the kinetics of the electrochemical device.

In a system of electrochemical devices, where the devices are interconnected in series and parallel connections, it is possible to measure the impedance of the entire system or of each individual unit.

The term system encompasses the term primary system.

The term electrochemical system encompasses the term secondary electrochemical system.

The electrochemical system may comprise any of batteries, fuel-cells, super capacitors, photo-electro-chemical-cells, and solar cells. A plurality of different electrochemical systems may be connectable or connected to the system simultaneously or sequentially.

In the context of the present invention the term connectable is to be understood as also comprising connected.

The power stage is adapted for supplying electrical energy to the electrochemical system, e.g. when the power stage is a charger, and/or for withdrawing electrical energy from the electrochemical system, e.g. when the power stage is an inverter or converter for supplying electrical energy from the electrochemical system to a consumer of the electrical energy.

The power stage comprises power electronics such as rectifiers, inverters, transformers, drivers, filters, etc. combined to enable power to be moved and/or converted between systems.

The Excitation Generation Unit (EGU) has the purpose of directly or indirectly controlling the power stage to generate the excitation signal. The Excitation Generation Unit may in some embodiments be adapted for instructing the power stage to generate the excitation signal by generating an intermediate excitation signal which is then delivered to the power stage and then amplified and or frequency-shifted by the power stage. In other embodiments the Excitation Generation Unit merely provides a basic step signal or other simple signal and the power stage generates the excitation signal. Thus the instruction from the Excitation Generation Unit to the power stage may be any of an intermediate signal having the intended waveform and/or frequency, but lacking the proper amplitude and/or frequency, to a basic step signal which the power stage detects and the generates the excitation signal.

The Excitation Generation Unit may be comprised by the power stage, i.e. be a part of the power stage, or may alternatively be connected to it as a separate unit.

The power stage may be adapted for generating the excitation signal by comprising controllable power electronics and/or by the power electronics comprising accessible terminals for setting parameters, such as for example output voltage or current, of the power electronics. Applying the signal or instruction to these terminals may then cause the power stage to vary its output to form the excitation signal. In the case of the power stage comprising controllable power electronics such as the power stage is controllable through a data bus, the Excitation Generation Unit may instruct the power stage to operate its power electronics in such a way as to generate the excitation signal.

The power stage may supply the excitation signal to the electrochemical system via a main power bus which is normally used when transferring electrical power from and/or to the electrochemical system. Alternatively the power stage may supply the excitation signal via a secondary power bus used only for supplying the excitation signal.

The electrochemical system may be connected to the system using a standard power cable or any standard connectors such as the IEC 62196 standard.

The instructing of the power stage, by the Excitation Generation Unit, may be deliberate as selected and initiated by a user of the system, or may be spontaneous according to the adaptation of the Excitation Generation Unit. The Excitation Generation Unit may for example be adapted for instructing the power stage to generate an excitation signal every time the electrochemical system is connected to the system.

Typically the power stage is a charger but other variants are possible.

Alternatively or additionally, the system itself may be a charger, inverter or converter, or the system may be a part of a charger, inverter or converter. The charger may be an AC to DC charger or a DC to DC charger. The power stage may supply electrical energy to the electrochemical system, for example where the system is a charger such as in a charging station for en electrical vehicle, or the power stage may withdraw electrical power from the electrochemical system, for example where the system is positioned onboard an electrical vehicle and the power stage is a power converter or power inverter in the drive train of the electrical vehicle.

By the advantageous embodiment of the system according to the first aspect of the present invention, a very cost effective implementation of Electrochemical Impedance Spectroscopy diagnostics is made possible for electric vehicles. The stationary charging station may for example be used to recharge a number of different electric vehicles. The electrochemical system may for example comprise one or more Lithium-ion batteries and the electrochemical system may be connectable to the charging station via a power cable and connector. The electrochemical system may be integrated with or in the electric vehicle, or alternatively the electrochemical system may be removable from the electric vehicle. The vehicle or the mobile device should be connectable to said stationary charging station for receiving electrical energy therefrom. Restated differently, a further aspect of the present invention may thus concern a stationary charging station comprising a system according to the first aspect of the present invention for charging a vehicle or mobile device comprising the electrochemical system.

By the advantageous embodiment of the system according to the first aspect of the present invention as defined in claim 8 a very cost effective implementation of Electrochemical Impedance Spectroscopy diagnostics is made possible for grid storage systems and residential energy storage systems. Thus a grid storage system comprising the system according to the first aspect of the present invention may be connected or connectable to a number of different electrochemical systems such as batteries, fuel-cells, super capacitors, solar cells, etc. while all of the electrochemical systems may be excited for Electrochemical Impedance Spectroscopy using a single Excitation Generation Unit.

Restated differently, a further aspect of the present invention may thus concern a grid storage system or residential energy storage system comprising a system according to the first aspect of the present invention.

In an alternative embodiment of the system according to the first aspect of the present invention the system is comprised by a vehicle or mobile device. This may be the case where the vehicle is designed to use transient electrochemical systems such as replaceable batteries or electrochemical systems in which an electrolyte is replenished after being used. Thus each set of replaceable batteries need not comprise all components needed for Electrochemical Impedance Spectroscopy diagnostics; rather cost is lowered by the system being comprised by the vehicle or mobile device.

The power stage may for example be an inverter or converter in the vehicle drive train, or a charger connected to the electrochemical system.

Restated differently, a further aspect of the present invention may thus concern a vehicle or mobile device comprising a system according to the first aspect of the present invention wherein the power stage is a part of the vehicle or mobile device drive train or power electronics connectable to the electrochemical system.

In order to obtain Electrochemical Impedance Spectroscopy diagnostics the system may further comprise a System Response Analyzer connected or connectable to the electrochemical system for measuring the response elicited by the excitation signal. Specifically it is the impedance of the electrochemical system which is measured by comparing the excitation signal (often a voltage signal) and the response signal (often a current signal). The System Response Analyzer may be adapted for determining diagnostics by comparing the measured impedance to previously stored impedance measurements, by directly evaluating the impedance for example by evaluating the appearance of a Nyquist plot of the imaginary part of the impedance vs. the real part of the impedance, or by using a circuit model of the electrochemical system. Parameters such as State-of-Charge (SoC), State-of-Health (SoH) and Remaining-useful-life (RUL) may be obtained by calculating the real and imaginary parts of the impedance and possibly representing the Impedance in a Nyquist plot, and then determining the SoH and/or SoC of the electrochemical system by curve fitting of a circuit model for the electrochemical system to the calculated real and imaginary parts of the impedance or the Nyquist plot.

The System Response Analyzer is connected to all, if several, electrochemical systems which are connected to the same power stage. Thus, if several electrochemical systems are connected to the same power stage the measured impedance, and therefore the determined Electrochemical Impedance Spectroscopy diagnostics, is representative for the total electrochemical systems.

In some embodiments the System further comprises a System Control Unit. The System Control Unit may comprise the System Response Analyzer or be connected to it for assisting in determining the diagnostics of the electrochemical system. The System Control Unit may for example be an already present System Control Unit controlling charging when the system is part of a charger.

Alternatively, or additionally, as defined in claim 9, an Individual Response Analyzer is comprised by, or connected to, the electrochemical system. This is advantageous as it provides for a more detailed measurement of the response signal and therefore a more detailed diagnostics. This is of special interest where more than one electrochemical system, or an electrochemical system comprising several electrochemical units, is connected or connectable to the system.

The above embodiments may be combined so that both a System Response Analyzer and one or more Individual Response Analyzers are used.

The Response Analyzer may determine the diagnostics by itself, or alternatively an Electronic Control Unit directly connected to the electrochemical system may work together with the individual response analyzed for determining the diagnostics.

The Electronic Control Unit may be an already present Battery Management System or other power electronics in or connected to the electrochemical system.

Furthermore the Individual Response Analyzer may be connectable to the System Control Unit (if present).

Typically the electrochemical system comprises a plurality of electrochemical devices and a plurality of Individual Response Analyzers. This makes it possible to determine Electrochemical Impedance Spectroscopy diagnostics for each individual electrochemical device and that thereby state-of-charge and can be more accurately determined and charge balancing of the electrochemical system may be performed more effectively.

Generally the electrochemical system comprises or is connected to an Electronic Control Unit. In these embodiments the Electronic Control Unit may comprise or be connected to the Individual Response Analyzer or the Individual Response Analyzers. The Electronic Control Unit may assist the Individual Response Analyzer(s) in determining the Electrochemical Impedance Spectroscopy diagnostics.

A further aspect of the present invention concerns an electrochemical infrastructure system as described herein.

Figure 2:
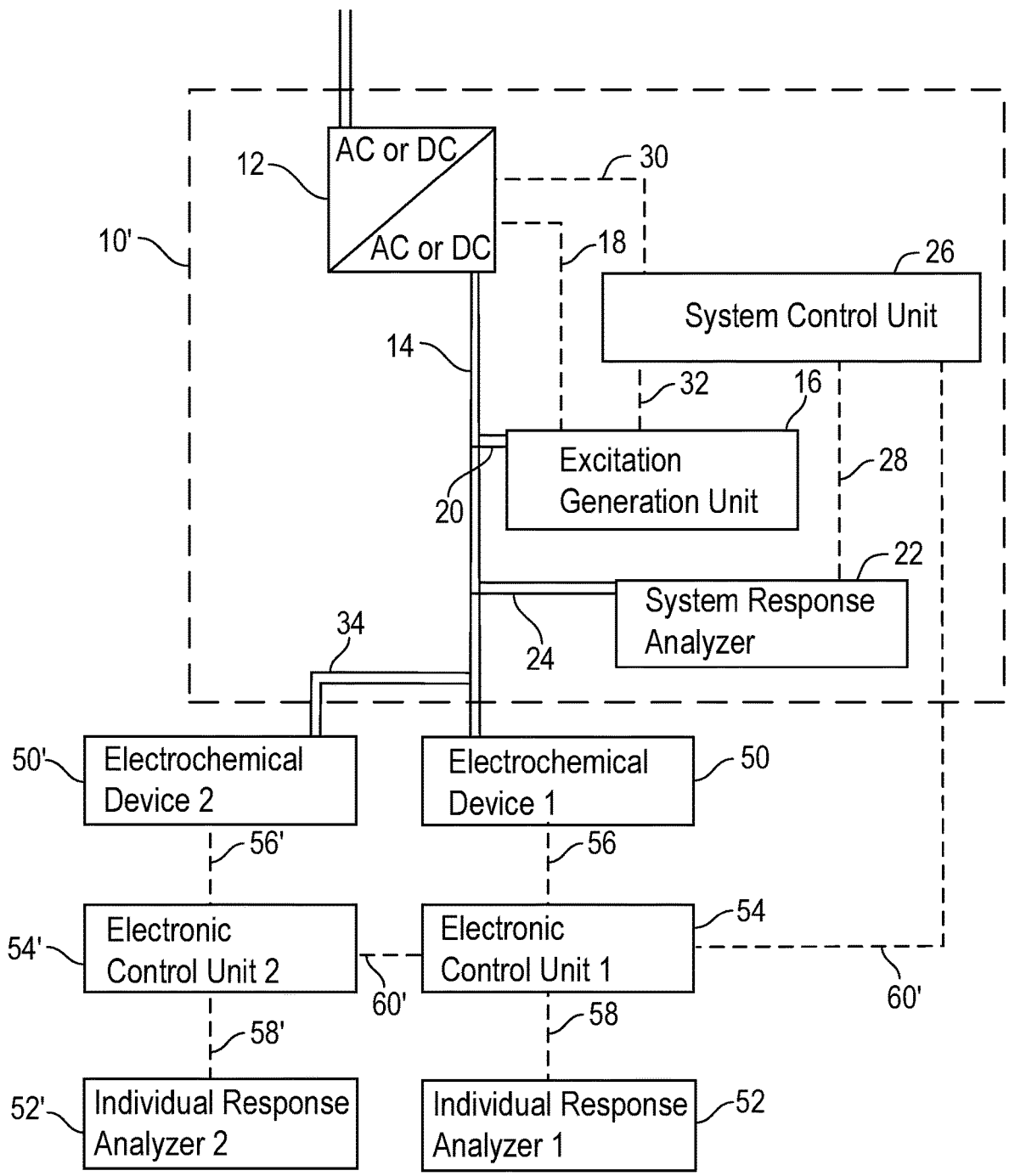

The invention and its many advantages will be described in more detail below with reference to the accompanying schematic drawings, which for the purpose of illustration show some non-limiting embodiments, and in which:

FIG. 1 shows a system and method for providing an excitation signal to an electrochemical system according to first embodiments of the first and second aspects of the present invention, and FIG. 2 shows a system and method for providing an excitation signal to an electrochemical system according to second embodiments of the first and second aspects of the present invention.

In the below description, one or more 'signs added to a reference number indicate that the element referred to has the same or similar function as the element designated the reference number without the 'sign, however, differing in structure.

When further embodiments of the invention are shown in the figures, the elements which are new, in relation to earlier shown embodiments, have new reference numbers, while elements previously shown are referenced as stated above. Elements which are identical in the different embodiments have been given the same reference numerals and no further explanations of these elements will be given.

FIG. 1 depicts a system 10 comprising a power stage 12 capable of providing AC or DC output. A main power bus 14 is connected to the power stage 12 and the power stage 12 is further connected to an Excitation Generation Unit (EGU) 16 via a first data bus 18, and to the main power bus 14 via a first power bus 20. The Excitation Generation Unit is adapted to instruct the power stage 12, via the first data bus 18, to generate an excitation signal on the main power bus 14, and the power stage is likewise adapted to be able for receiving the instruction from the Excitation Generation Unit 16 and to generate and emit the desired excitation signal. The excitation signal can either be produced on top of the output from the power stage 12, or as a separate signal.

The system 10 described thus far comprises all necessary components for providing an excitation signal to an electrochemical system.

Thus a first electrochemical system or device 50 may as is shown in FIG. 1 be connected to the main power bus 14 for receiving electrical power from the power stage 12. Typically the system 10 is part of or comprised by a charger for the electrochemical system 50 such that the power stage 12 provides electrical energy to the electrochemical system 50 via main power bus 14 for charging the electrochemical system 50.

In order to obtain Electrochemical Impedance Spectroscopy diagnostics for the first electrochemical system or device 50 a Response Analyzer is needed for measuring the response signal of the electrochemical system 50 to the excitation signal from the Excitation Generation Unit. In the simplest implementation this Response Analyzer is implemented by a System Response Analyzer 22 connected to the main power bus 14 via second power bus 24. The System Response Analyzer 22 may, as shown in FIG. 1, be separate from the Excitation Generation Unit 16, or alternatively it may be a part of it.

The System Response Analyzer 22 measures the excitation signal, and the response signal that is elicited by the excitation signal from the first electrochemical system or device 50, on the main power bus 14 and determines the impedance from the measurements. The measured impedance may be further treated by the System Response Analyzer 22 for determining a parameter of the first electrochemical device or system 50, or alternatively a System Control Unit (SCU) 26 is included in the system 10 for determining the parameters. For this purpose the System Control Unit 26 is connected to the System Response Analyzer 22 via a second data bus 28. The system Control Unit 26 may have further functions such as controlling the power stage 12 via third data bus 30, for example for controlling the charging of the first electrochemical device or system 50, and for controlling the Excitation Generation Unit 16 via a fourth data bus 32 for controlling when and how the Excitation Generation Unit 16 instructs the power stage 12 to generate and send out an excitation signal on the main power bus 14.

Although the system 10 as described so far provides a cost effective way of obtaining Electrochemical Impedance Spectroscopy diagnostics on a first electrochemical system or device 50 connected to the systems 10 main power bus 14, the response measured and thus the impedance and diagnostics determined concern only the total connected first electrochemical system or device 50. In particular where a plurality of different electrochemical devices or systems 50 are connected simultaneously to the main power bus 14, or where the electrochemical device or system 50 comprises a plurality of individual units such as battery cells, capacitors, etc., there may arise a need to determine the response of each of these individual units separately.

This may be obtained in a cost effective way by providing, in the first electrochemical device or system 10, or connected thereto, Individual Response Analyzers 52, one for each electrochemical device 50, or unit thereof. Cost is still minimized since there is still only a single Excitation Generation Unit 16 and single power stage 12 used. Preferably, as shown in FIG. 1, in this case the first electrochemical device or system 50 comprises or is connected to a first Electronic Control Unit (ECU) 54 which is connected to the first electrochemical device or system 50 and the Individual Response Analyzer 52 via fifth and sixth data buses 56 and 58, respectively.

The Electronic Control Unit 54 may be existing hardware, such as a battery management system, fuel cell management or super capacitor stacks management system, or a dedicated hardware specifically designed for acquiring the individual responses of the electrochemical devices or systems 50 or units thereof.

Obtaining Electrochemical Impedance Spectroscopy diagnostics for individual electrochemical devices or systems 50 may for example be used for load balancing and charge balancing between the individual electrochemical devices or systems 50 or units.

The individual response signal measured by the Individual Response Analyzer 52 may be used to determine an impedance and diagnostics by the Individual Response Analyzer 52 alone or together with the Electronic Control Unit 54, or alternatively or additionally the result of the diagnostics or the impedance or other measurement is sent to the System Control Unit 26 via seventh data bus 60.

Both System Response Analyzer 22 and Individual Response Analyzer 52 may be used at the same time to obtain diagnostics with different level of detail.

Some of the main advantages of the present invention are readily apparent from studying FIG. 1. Thus, in a common implementation the system 10 is, or is part of, a stationary charger for an electrical vehicle. The electrical vehicle carries the first electrochemical device or system 50 and connects to the main power bus 14 when in need of recharging the first electrochemical device or system 50. The System Control Unit 26 in the system 10, or indeed the Excitation Generation Unit 16 itself may be programmed or adapted to, before, during, or after the first electrochemical device or system 50 has been fully charged, cause the power stage 12 to generate and send out an excitation signal on the main power bus 14 for obtaining a response signal from the first electrochemical system or device 50.

Electrochemical Impedance Spectroscopy diagnostics may then be obtained by the System Response Analyzer 22 together with the System Control Unit 26 and presented to the driver of the electrical vehicle carrying the first electrochemical device or system 50 by the charger.

Alternatively or additionally the diagnostics may be obtained by the Individual Response Analyzer 52 and presented by the electric vehicle's Electronic Control Unit 54. The diagnostics may be used to provide the driver of the electric vehicle with an accurate state-of-charge, state-of-health and remaining-useful life of the first electrochemical device or system 50 in the electric vehicle, and may further be uploaded to a fleet manager managing a plurality of electrical vehicles for detecting electrical vehicles in need of a replacement first electrochemical device or system 50.

The same advantages may apply also for fuel filling stations for fuels for electrochemical devices or systems such as fuel cells. Thus a single Excitation Generation Unit and power stage may be used to obtain diagnostics on fuel cells in a large fleet of fuel cell powered vehicles.

The system 10 may also be used with stationary applications such as for grid storage. Thus where the power stage 12 is an inverter Electrochemical Impedance Spectroscopy diagnostics can be obtained from a pack of electrochemical systems 50 such as super capacitors, batteries, fuel cells or solar cells. By implementing the Excitation Generation Unit in or connected to the inverter it is possible to obtain diagnostics on several packs of different types of electrochemical systems with a single Excitation Generation Unit 16, thus saving costs.

This embodiment is shown in FIG. 2 in which first and second different electrochemical devices or systems 50 and 50', for example batteries, fuel cells, super capacitors or other electrochemical devices, are connected to the main power bus 14, the second electrochemical device or system 50' being connected via a main power bus branch 34. Also the Electronic Control Units 54 and 54', and the Individual Response Analyzers 52 and 56' may be different.

In the above and other embodiments of the present invention the following parameters comprised by the diagnostics provided by Electrochemical Impedance Spectroscopy may be determined and monitored.

State-of-charge—Using Electrochemical Impedance Spectroscopy the State-of-charge of batteries and super capacitors can be estimated for better balancing of pack of cells, see Huet F. mentioned above.

State-of-health and degradation measurement can be used to monitor the health and degradation of electrochemical cells, see Jensen, S. H., Hauch, A., Knibbe, R., Jacobsen, T. & Mogensen, M., and Huet, F. mentioned above. See also Ecker, M., Nieto, N., Käbitz, S., Schmalstieg, J., Blanke, H., Warnecke, A., & Sauer, D. U. *Calendar and cycle life study of Li(NiMnCo)O2-based 18650 lithium-ion batteries*. Journal of Power Sources, 248(C), 839-851. (2014), and Waag, W., Käbitz, S., & Sauer, D. U. *Experimental investigation of the lithium-ion battery impedance characteristic at various conditions and aging states and its influence on the application*. Applied Energy, 102, 885-897 (2013).

State-of-Charge, State-of-health, and other charge and degradation parameters as well as currentvoltage characteristics for electrochemical cells and packs can be used for fleet management in transient systems, e.g. electrical vehicles and/or management of an array of stationary systems.

The system 10 also allows for sophisticated current profiles being controlled through the either the system control unit (SCU) or EGU, e.g. as seen in Bertness, K. I. and McShane, S. J. *Method and apparatus for charging a battery*. U.S. Pat. No. 6,081,098, and Cope, R. C.; Podrazhansky, Y., *The art of battery charging* Battery Conference on Applications and Advances, 233-235 (1999).

LIST OF PARTS WITH REFERENCE TO THE FIGURES

10. System for providing an excitation signal to an electrochemical system
12. Power stage
14. Main power bus 16. Excitation Generation Unit (EGU)
18. First data bus
20. First power bus
22. System Response Analyzer (SRA)
24. Second power bus
26. System Control Unit (SCU)
28. Second data bus
30. Third data bus
32. Fourth data bus
34. Main power bus branch
50. First Electrochemical Device or system
52. First Individual Response Analyzer (IRA)
54. First Electronic Control Unit (ECU)
56. Fifth data bus
58. Sixth data bus
60. Seventh data bus

The invention claimed is:

1. An electrochemical infrastructure system for an electrical vehicle, comprising:
   an electrochemical system;
   an electrical vehicle having a vehicle system providing an excitation signal to the electrochemical system for use in Electrochemical Impedance Spectroscopy diagnostics on the electrochemical system;
   the electrochemical system being connectable to the vehicle system;
   the vehicle system comprising a power stage being a charger for the electrochemical system and connectable to the electrochemical system for supplying electrical energy to the electrochemical system, the power stage comprising an Excitation Generation Unit, the power stage being a part of a vehicle drive train or power electronics connectable to the electrochemical system;
   the electrochemical system further comprising an individual Response Analyzer operable to measure an impedance of the electrochemical system in response to the excitation signal, the Individual Response Analyzer further being adapted for determining diagnostics of the electrochemical system based on the impedance;
   the Excitation Generation Unit being adapted for instructing the power stage, the power stage acting as a charger, to generate the excitation signal for use in the Electrochemical Impedance Spectroscopy diagnostics; and
   the power stage being adapted for generating the excitation signal and supplying the excitation signal to the electrochemical system when so instructed by the Excitation Generation Unit.

2. The electrochemical infrastructure system according to claim 1, wherein the charger is an AC to DC charger.

3. The electrochemical infrastructure system according to claim 1, wherein the charger is a DC to DC charger.

4. The electrochemical infrastructure system according to claim 1, wherein the power stage is a power converter for the electrochemical system.

5. The electrochemical infrastructure system according to claim 1, further comprising:
   a System Response Analyzer for measuring the impedance of the electrochemical system in response to the excitation signal, the System Response Analyzer further being adapted for determining diagnostics of the electrochemical system based on the impedance.

6. The electrochemical infrastructure system according to claim 5, wherein the System Response Analyzer comprises the Excitation Generation Unit.

7. The electrochemical infrastructure system according to claim 1, wherein the electrochemical system comprises a plurality of electrochemical devices and a plurality of the Individual Response Analyzers, each Individual Response Analyzer being associated with a corresponding one of the plurality of electrochemical devices.

8. The electrochemical infrastructure system according to claim 1, wherein the electrochemical system comprises or is connected to an Electronic Control Unit, the Electronic Control Unit comprising or being connected to the Individual Response Analyzer.

9. A method of providing an excitation signal to an electrochemical system for an electrical vehicle for use in Electrochemical Impedance Spectroscopy diagnostics on the electrochemical system, comprising the steps of:
   providing an electrochemical infrastructure system according to claim 1;
   connecting an electrochemical system to the vehicle system;
   instructing the power stage, by the Excitation Generation Unit, to generate the excitation signal for use in the Electrochemical Impedance Spectroscopy diagnostics; and
   generating and supplying the excitation signal to the electrochemical system by the power stage.

* * * * *